United States Patent [19]
Berthiaume et al.

[11] Patent Number: 6,110,146
[45] Date of Patent: Aug. 29, 2000

[54] PROTECTOR FOR CATHETER BALLOON WITH GUIDEWIRE BACKLOADING SYSTEM

[75] Inventors: William A. Berthiaume, Hudson; Nareak Douk, Lowell, both of Mass.

[73] Assignee: Medtronic AVE, Inc., Santa Rosa, Calif.

[21] Appl. No.: 09/164,166

[22] Filed: Sep. 30, 1998

[51] Int. Cl.⁷ .................................................. A61M 5/178

[52] U.S. Cl. ............................. 604/160; 604/96; 604/103

[58] Field of Search ................................ 604/160, 96, 103, 604/523, 912, 915, 917

[56] References Cited

U.S. PATENT DOCUMENTS

| | | | |
|---|---|---|---|
| 4,895,565 | 1/1990 | Hillstead | 604/167 |
| 4,921,479 | 5/1990 | Grayzel | 604/53 |
| 5,015,231 | 5/1991 | Keith et al. | 604/96 |
| 5,352,236 | 10/1994 | Jung et al. | 606/194 |
| 5,425,710 | 6/1995 | Khair et al. | 604/96 |
| 5,871,444 | 2/1999 | Ouchi | 600/374 |

*Primary Examiner*—Mark O. Polutta
*Assistant Examiner*—Jeremy Thissell
*Attorney, Agent, or Firm*—Sterne, Kessler, Goldstein & Fox PLLC

[57] ABSTRACT

A balloon protector for the balloon of a dilatation catheter includes a distally extending flared section that defines a funnel receptive to a guidewire in order to facilitate backloading of the guidewire into the catheter.

9 Claims, 2 Drawing Sheets

PROTECTOR FOR CATHETER BALLOON WITH GUIDEWIRE BACKLOADING SYSTEM

FIELD OF THE INVENTION

The invention relates to balloon dilatation catheters that are used with movable guidewires.

BACKGROUND OF THE INVENTION

Balloon dilatation catheters are used in a variety of medical procedures. One such procedure involves percutaneous transluminal angioplasty (PTA) and, particularly, percutaneous transluminal coronary angioplasty (PTCA), in which a balloon is used to dilate an obstructed artery. The PTCA procedure typically involves the use of a very slender, low profile balloon catheter in conjunction with a small diameter steerable guidewire. The guidewire can be manipulated and navigated to and into the coronary arteries to the location of a narrowed arterial portion that is to be dilated with the balloon of the catheter. With the guidewire in place, the catheter then can be advanced over the guidewire to the site of the obstruction. The catheter is advanced to place the balloon within the obstruction and the balloon then is inflated under high pressure to forcibly dilate that region of the artery. The procedure serves to widen the flow passage to permit more effective blood flow through the artery.

Balloon angioplasty catheters typically are used in arteries that are narrow, such as the coronary arteries, and in circumstances where the naturally narrow artery is even further narrowed by the obstruction (stenosis). It is essential, in order to perform the procedure, for the balloon to have a low profile, that is, a small effective deflated cross-sectional diameter so that it can be advanced into the stenosis. To that end, the balloon of the angioplasty catheter typically is formed from a very thin polymeric material that can be wrapped closely about the shaft of the catheter to minimize the profile. Although an undamaged balloon is capable of developing high pressures under inflation, the balloons are delicate and may be susceptible to minor scratches or other damage, as during handling, that could result in premature balloon failure. Consequently, it is a common practice to enclose the balloon portion of the catheter in a sleeve-like balloon protector that is not removed until the catheter is set-up for use by the physician. The balloon protector also may serve to maintain the balloon in its tightly wrapped, low profile configuration during shipment and storage. Examples of some balloon protectors are described in U.S. Pat. Nos. 4,573,470 (Samson), 4,930,341 (Euteneuer), 5,015,231 (Keith), 5,053,007 (Euteneuer), 5,066,298 (Hess), 5,342,307, (Euteneuer), 5,352,236 (Jung), 5,417,707 (Parkola), 5,425,710 (Khair), 5,569,294 (Parkola), and EP 0 744 187 A1 (Klunder).

Another aspect of balloon dilatation catheters, normally unrelated to balloon profile or protection, is that when the catheter is set up for insertion into the patient, the guidewire typically is preloaded into the catheter so that the two can be inserted into the patient's vasculature together. The catheter is provided with a lumen extending longitudinally through which the guidewire is received. The guidewire lumen typically terminates at a distal outlet orifice at the distal tip of the catheter, slightly beyond the distal end of the balloon. After the catheter and guidewire are together inserted into the vasculature, the guidewire then is projected forwardly to the intended site of treatment, as described above, after which the catheter can be advanced over the guidewire to place the balloon at the intended site. The procedure for loading the guidewire into the catheter can present some difficulties. A common technique for loading the guidewire into the guidewire lumen of the catheter is to "backload" the guidewire, that is, to insert the proximal end of the guidewire into the distal outlet orifice at the distal tip of the catheter. The guidewire then is fed proximally through the guidewire lumen until the proximal end of the guidewire emerges from the proximal end of the catheter. Backloading the guidewire into the distal end of the guidewire lumen of the catheter is the only practical way to advance a catheter onto the guidewire that is already in place in the patient, as may occur when the original catheter is to be exchanged with another catheter. The second catheter can only be backloaded onto the proximal end of the guidewire because that is the only end that is accessible outside of the patient. The typically small dimensions of the guidewire, the catheter tip and the distal outlet orifice, coupled with the relatively delicate nature of these components, can present some difficulty in the backloading procedure. By way of example, a guidewire diameter used in PTCA procedures typically can have a diameter of 0.010 to 0.018 inch. The guidewire lumen in the catheter has a diameter slightly greater than the guidewire. The distalmost tip of the catheter shaft, at the distal outlet orifice may be tapered slightly to present an even narrower clearance with the guidewire.

It is among the general objects of the invention to provide a device that serves to protect the balloon while also facilitating backloading of the guidewire into the guidewire lumen of the catheter.

SUMMARY OF THE INVENTION

In one embodiment of the invention, the balloon protector is in the form of an elongate tube adapted to be disposed about the wrapped balloon. The distal end of the protector is flared to define a funnel-like configuration. The protector is configured and dimensioned so that the portions proximal of the funnel will enclose and protect the balloon. When placed on the catheter, the funnel is positioned so that its narrow end is at the distal outlet orifice of the guidewire lumen. The protector also is provided with a slit that extends the full length of the protector. When the catheter is set up for use, the proximal end of the guidewire is inserted into the open funnel that, in turn, guides the end of the wire to and into the distal orifice of the guidewire lumen. After the guidewire has been loaded into the catheter, the protector can be slid distally off of the catheter and onto the guidewire, from which the protector can be peeled off, through the slit. The ability to remove the balloon protector from the catheter enables the device to be used when a catheter is backloaded onto a guidewire wire that has previously been placed in the patient, as during a catheter exchange, where the distal end of the guidewire is within the patient and is inaccessible.

In another embodiment, the slit, funneled tube protector is provided with an outer tube that serves to enhance the constriction of the inner tube about the prewrapped balloon. The outer tube can be slid or rolled off preliminarily to backloading of the catheter onto the guidewire.

It is among the general objects of the invention to provide an improved technique for preliminarily preparing and storing a balloon dilatation catheter in readiness for set-up and use by the physician. Also among the objects of the invention are to provide a combined balloon protector and guidewire backloading aid; to provide a device which is adapted for use both with an initially placed catheter as well as a successive catheter used in a catheter exchange procedure and to provide improved techniques for storing and setting up balloon dilatation catheters. By way of example, a catheter exchange procedure is described in U.S. Pat. No. 4,922,923 (Gambale), the disclosure of which is incorporated herein by reference, in its entirety.

BRIEF DESCRIPTION OF THE DRAWINGS

The foregoing and other objects and advantages of the invention will be appreciated more fully from the following further description thereof, with reference to the accompanying diagramatic drawings wherein.

DESCRIPTION OF THE ILLUSTRATIVE EMBODIMENTS

Figure 1:
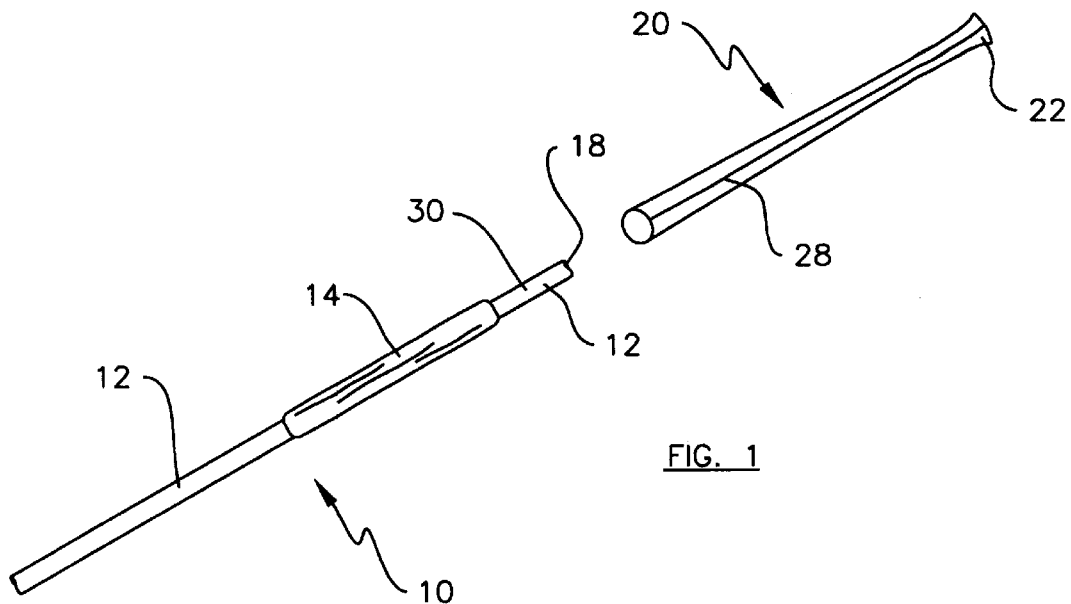
FIG. 1 is an illustration of the distal end of a catheter having a wrapped balloon and an axially spaced balloon protector in accordance with the invention in readiness to receive the balloon.

FIG. 1 illustrates the distal end (the end inserted into the patient) of a balloon dilatation catheter 10. The catheter 10 includes elongate flexible shaft 12. The shaft has two lumens (not shown in detail), one of which extends from the proximal end (the end outside of the patient) and communicates with the interior of a balloon 14 mounted on the distal region of the shaft 12 to enable inflation and deflation of the balloon. The shaft 12 also includes a guidewire lumen (not shown) adapted to receive a slender guidewire 16. The guidewire lumen terminates at the distal tip of the catheter shaft 12 in an outlet orifice 18 from which the guidewire can extend.

The balloon 14 may be formed from a variety of materials in order to provide different characteristics as may be desired for a particular procedure. By way of example only, one such balloon is described in U.S. Pat. No. Re. 32,983, the disclosure of which is incorporated herein by reference, in its entirety. During manufacture of the balloon, the balloon typically is evacuated to form flattened wings or flutes that can be wrapped about the catheter shaft 12. The balloon preferably is wrapped tightly so that it will present a low effective diameter (low profile) that will facilitate its advancement and entry into the stenosed region of the blood vessel to be treated. Although the balloon may be capable of withstanding substantial inflation pressures, its surface generally is treated as delicate in order to avoid damage that might result in a stress risers, leading to premature failure. To that end, after the balloon is wrapped, it is common to place a balloon protector about the balloon, the protector typically being in the form of an elongate sleeve adapted to slip over and contain the balloon in its wrapped configuration. The sleeve is not removed until the catheter is intended to be used by the physician.

Figure 2:
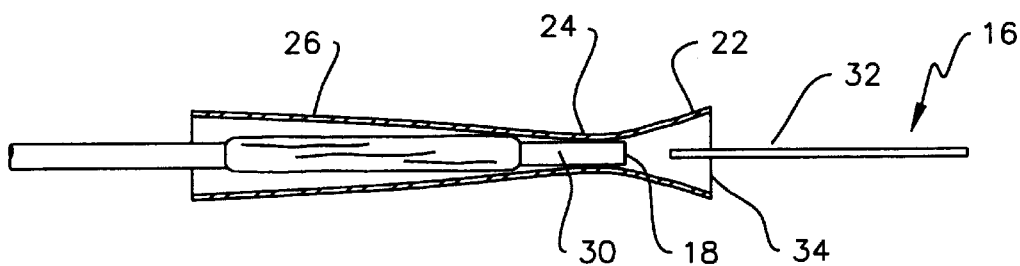
FIG. 2 is a cross-sectional illustration of the assembled sleeve and the balloon with the proximal end of a guidewire adjacent the distal end of the sleeve in readiness to be backloaded into the guidewire lumen of the catheter.

In accordance with the present invention a balloon protector 20 is formed in a generally tubular configuration with a funnel-like flared distal end 22. The flared end 22 communicates with a narrowed neck 24 that, in turn, leads to a proximal balloon protector segment 26. The protector 20 is formed with a longitudinally extending slit 28 that extends fully from the proximal end to the distal end of the device. In the embodiment shown in FIG. 1, the slit is essentially straight. The flared distal end, 22, neck 24 and protector segment 26 are dimensioned so that when the protector segment 26 is slipped proximally over the balloon, the distal tip 30 of the shaft 12 will be contained within the neck 24 and in a position so that the distal outlet orifice 18 is disposed at the narrow region of the funnel. The protector segment 26 extends proximally from the neck and should be long enough to extend over the full length of the balloon, completely protecting and covering it. With most balloon dilatation catheters, the proximal neck of the balloon is attached to a larger diameter portion of the shaft than is the distal end of the balloon. Consequently, the proximal cone of the balloon, when wrapped to its low profile, will tend to have a larger effective cross-sectional dimension than the distal cone. In order to accommodate the differences in profiles of the cones, the protector segment 26 preferably is configured to have a smaller effective diameter at its distal region than at its proximal portion. The protector segment 26 may be tapered, the degree of taper being selected to closely surround the wrapped balloon while permitting the protector to be slipped on to and off of the balloon with relatively ease. In catheters where there is little or no difference in the profile of the proximal and distal cones, the protector segments 26 may have very little if any taper. After the catheter has been fabricated, the protector 20 is slipped over the distal end of the catheter as shown in FIG. 2. In that configuration, the assembly is ready to receive the proximal end 32 of a guidewire 16. The guidewire may be completely external of the patient or may be indwelling in the patient, with the catheter being used, for example, as a secondary catheter in a catheter exchange procedure. The invention facilitates the backloading of the guidewire into the distal orifice 18 of the catheter. The relatively large opening 34 at the distal end of the flared end 22 can easily receive the proximal end 32 of the guidewire. The funnel-like interior of the flared end 22 guides the proximal end of the guidewire to the distal orifice 18 of the catheter thereby avoiding the difficulties presented in aligning and inserting the proximal end of the guidewire into the orifice 18.

Figure 3:
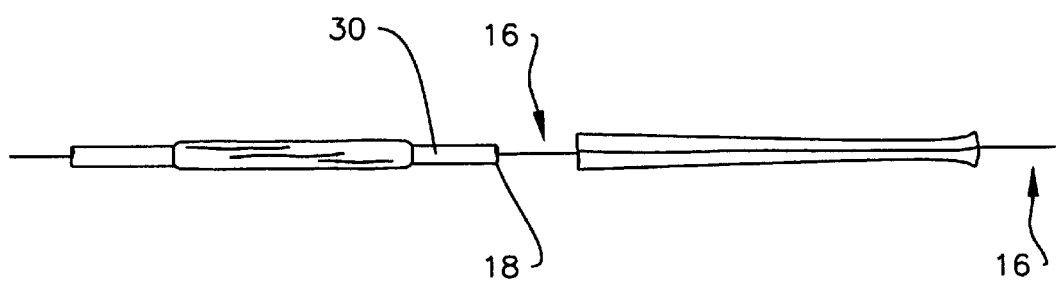
FIG. 3 is an illustration of the device after the guidewire has been backloaded and with the sleeve having been advanced distally off of the catheter and onto the guidewire.
Figure 4:
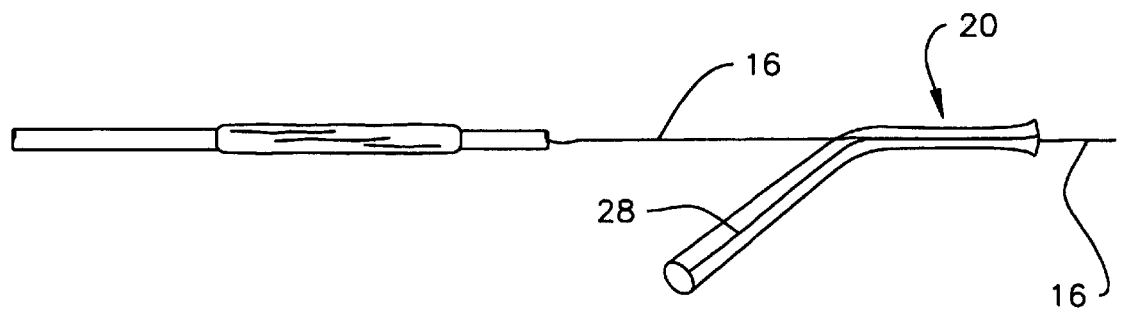
FIG. 4 is an illustration of the protector during transverse removal from the guidewire with the protector being partly peeled off of the guidewire.
Figure 5:
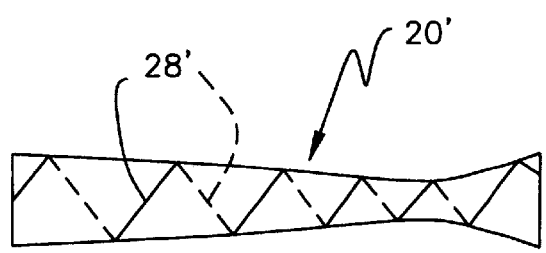
FIG. 5 is an illustration of a balloon protector in accordance with the invention in which the protector is provided with a helical slit.

After the guidewire 16 has been backloaded into the guidewire lumen of the catheter shaft 12 and has been advanced sufficiently to assure that the guidewire 16 is retained within the guidewire lumen, the protector 20 then may be slid off of the balloon catheter in a distal direction to a position as shown in FIG. 3, in which the protector 20 is disposed on the guidewire, distally of the catheter. The protector 20 then may be removed, as suggested in FIG. 4, by slipping it transversely off of the wire 16, with the guidewire 16 passing through the longitudinal slit 28. With the protector 20 removed, the procedure can be continued in a normal fashion. FIG. 5 illustrates a modified embodiment of the balloon protector 20' which is identical to the protector 20 except that the slit 28' is formed helically along the length of the protector.

The protectors 20, 20' may be formed from a suitable polymeric material such as polyethylene, polypropylene, fluorocarbon polymers or like biocompatible materials. The protector 20, 20' preferably have a minimum internal diameter equal to or greater than about 0.014" and a minimum outer diameter, at the neck, equal to or greater than about 0.054". The length should be sufficient to extend over the full length of the balloon when the device is used as described above. For example, the overall length of the device may be between 70 and 80 mm with the flared distal end 22 extending over 5 to 10 mm. The inner diameter of the protectors 20, 20' may be of the order of 0.044" at the mouth 34 of the flared distal end 22 and at the proximal end of the protector segment 26. The outer diameter of the protector at those regions may be of the order of 0.090".

Figure 6:
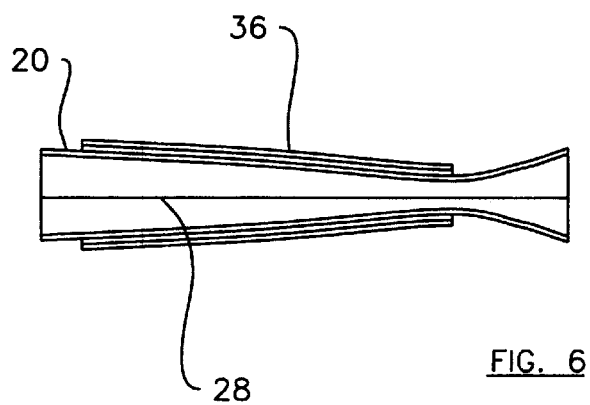
FIG. 6 is an illustration of another embodiment of the invention in which the device is provided with an outer, second sleeve.

FIG. 6 illustrates, diagramatically, a modified embodiment in which the protector 20 is provided with a second, outer polymeric tube 36. The outer tube 36 may be formed from an elastomeric polymer (e.g. latex, silicon, Kraton™ or the like.) The outer tube 36 preferably has the same shape as the protector segment 26 of the protector 20. The outer tube 36 also should have a length greater than that of the balloon, although the outer tube 36 may be shorter than the protector 20. The device is arranged so that the flared end 22 of the protector 20 will extend beyond the distal end of the outer tube 36. When the elastomeric outer tube 36 is used it serves to maintain that the slit 28 of the protector 20 fully closed. When the catheter is to be used, the outer tube 36 can be slid or rolled off of the inner protector 20. The physician then can backload the proximal end of the guidewire into the distal orifice 18, guided by the funnel-like flared end 22 of the protector. The procedure is then completed as described above.

From the foregoing it will be appreciated that the invention enhances and facilitates setting up of balloon catheters that are used with a guidewire, particularly where it is desired to backload the guidewire into the guidewire lumen of the catheter. The invention achieves this objective while also serving as a balloon protector. The backloading can be achieved without the use of supplemental guiding devices. It should be understood, however, that the foregoing description of the invention is intended merely to be illustrative thereof and that other embodiment, modification and equivalents may be apparent to those skilled in the art.

Having thus described the invention what we desire to claim secure by letters patents is:

1. A protective sleeve for a balloon dilatation catheter comprising:

an elongate tubular member having a neck portion and a slit extending along the entire length of the tubular member from a proximal end to a distal end thereof, wherein a distal portion of the tubular member is flared from the neck portion to the distal end of the tubular member to define an enlarged funnel-like opening.

2. A protective sleeve as defined in claim 1, wherein the slit extends along a plane that includes a longitudinal axis of the tubular member.

3. A protective sleeve as defined in claim 1 wherein the slit is helical.

4. A protective sleeve as defined in claim 1 further comprising:

an outer sleeve disposed about those portions of the tubular member proximal of the flared distal portion, the outer sleeve being configured to maintain the slit of the tubular member in a closed configuration.

5. A protective sleeve as defined in claim 4 wherein the outer sleeve is elastomeric.

6. A balloon catheter and a protective sleeve for the balloon of the catheter comprising, in combination:

a catheter having a shaft and a balloon mounted thereon, wherein the shaft has a distal tip portion that extends distally beyond a distal extremity of the balloon; and a protective sleeve as defined in claim 1, wherein a proximal portion of the sleeve is disposed about and encloses the balloon, the sleeve being mounted on the catheter to locate the distal tip portion of the catheter at the narrowest portion of the funnel defined by the flared distal portion of the tubular member whereby a guidewire backloaded through the flared distal portion will be guided into registry with the distal tip of the catheter shaft.

7. A method for backloading a guidewire into a balloon dilatation catheter comprising:

providing a protective sleeve as defined in claim 1;

placing a proximal portion of the protective sleeve about the balloon of the catheter, with the balloon having been preliminarily wrapped to a low profile configuration;

positioning a distal tip of the catheter at the apex of the funnel-like opening; and backloading a proximal end of the guidewire through the funnel-like opening into a distal orifice of the catheter.

8. A method as defined in claim 7 further comprising:

sliding the protective sleeve distally off of a distal end of the catheter and onto the guidewire; and removing the protective sleeve from the guidewire by passing the guidewire transversely through the slit.

9. A method as defined in claim 7 further comprising:

applying a constriction about the protective sleeve to maintain the slit in its closed configuration;

removing the constriction before backloading the guidewire into the catheter.

* * * * *